United States Patent
Sakamoto et al.

(10) Patent No.: US 12,188,090 B2
(45) Date of Patent: Jan. 7, 2025

(54) METHOD FOR DISCRIMINATING SEX OF YELLOWTAIL GROUP

(71) Applicant: National University Corporation Tokyo University of Marine Science and Technology, Tokyo (JP)

(72) Inventors: Takashi Sakamoto, Tokyo (JP); Masatoshi Nakamoto, Tokyo (JP); Kiyoshi Kikuchi, Tokyo (JP); Takashi Koyama, Tokyo (JP)

(73) Assignee: National University Corporation Tokyo University of Marine Science and Technology, Tokyo (JP)

( * ) Notice: Subject to any disclaimer, the term of this patent is extended or adjusted under 35 U.S.C. 154(b) by 1085 days.

(21) Appl. No.: 16/970,697

(22) PCT Filed: Feb. 18, 2019

(86) PCT No.: PCT/JP2019/005821
§ 371 (c)(1),
(2) Date: Oct. 26, 2020

(87) PCT Pub. No.: WO2019/160136
PCT Pub. Date: Aug. 22, 2019

(65) Prior Publication Data
US 2021/0032697 A1 Feb. 4, 2021

(30) Foreign Application Priority Data
Feb. 19, 2018 (JP) .................................. 2018-027260

(51) Int. Cl.
*C12Q 1/6879* (2018.01)
(52) U.S. Cl.
CPC ..... *C12Q 1/6879* (2013.01); *C12Q 2600/124* (2013.01); *C12Q 2600/156* (2013.01)
(58) Field of Classification Search
None
See application file for complete search history.

(56) References Cited

FOREIGN PATENT DOCUMENTS

| JP | 2010-226974 A | 10/2010 |
|---|---|---|
| JP | 2014-180233 A | 9/2014 |

OTHER PUBLICATIONS

Koyama et al Current Biology. May 23, 2019. 29: 1901-1909 and Supplemental Information, 24 pages total (Year: 2019).*
GenBank Reference Sequence XM_023413720.1, NCBI Database, National Library of Medicine, available via URL: < ncbi.nlm.nih.gov/nuccore/XM_023413720.1>, Dec. 26, 2017 (Year: 2017).*
NIH BioProject PRJNA423295, National Library of Medicine, "Seriola lalandi dorsalis" available via URL: < ncbi.nlm.nih.gov/bioproject/PRJNA423295>, Dec. 8, 2017 (Year: 2017).*
Communication, dated Jan. 7, 2022, issued by the Japanese Patent Office in corresponding Japanese Application No. 2018-027260.
International Preliminary Report on Patentability, dated Sep. 3, 2020, issued by the International Bureau in International Application No. PCT/JP2019/005821.
Catherine M. Purcell et al., "Insights into teleost sex determination from the *Seriola dorsalis* genome assembly", BMC Genomics, 2018, 19:31, 12 pages.
Takashi Koyama et al., "Identification of Sex-Linked SNPs and Sex-Determining Regions in the Yellowtail Genome", Mar Biotechnol (2015), vol. 17, pp. 502-510.
Kanako Fuji et al., "Identification of the sex-linked locus in yellowtail, *Seriola quinqueradiata*", Aquaculture, 2010, pp. 551-555, vol. 308.
Junya Kawase et al., "Identification of Sex-associated SNPs of Greater Amberjack (*Seriola dumerili*)", Journal of Genomics, 2018, vol. 6, pp. 53-62.
International search report for PCT/JP2019/005821, dated May 14, 2019.

* cited by examiner

*Primary Examiner* — Carla J Myers
(74) *Attorney, Agent, or Firm* — Sughrue Mion, PLLC

(57) ABSTRACT

Disclosed is a method for determining the sex of yellowtails, the method comprising a step of identifying whether an amino acid residue at position 143 in polypeptide encoded by the HSD17B1 gene of yellowtails is a glutamic acid residue or a glycine residue; a nucleic acid molecule or a primer set which is for use in said method; or a kit comprising the same, for determining the sex of yellowtails. The method according to the present invention is useful in that the genetic sex of yellowtails can be accurately determined.

3 Claims, 1 Drawing Sheet

Specification includes a Sequence Listing.

R:A/G

Reference sequence (SEQ ID NO: 14)

Female:
- Kanpachi (SEQ ID NO: 15)
- Kanpachi (SEQ ID NO: 15)
- Kanpachi (SEQ ID NO: 15)
- Kanpachi (SEQ ID NO: 15)
- Kanpachi (SEQ ID NO: 15)
- Hiramasa (SEQ ID NO: 15)
- Hiramasa (SEQ ID NO: 15)
- Hiramasa (SEQ ID NO: 15)
- Hiramasa (SEQ ID NO: 16)
- Hiramasa (SEQ ID NO: 15)
- Buri (SEQ ID NO: 17)
- Buri (SEQ ID NO: 17)
- Buri (SEQ ID NO: 17)
- Buri (SEQ ID NO: 17)
- Buri (SEQ ID NO: 17)

Male:
- Kanpachi (SEQ ID NO: 18)
- Kanpachi (SEQ ID NO: 18)
- Kanpachi (SEQ ID NO: 18)
- Kanpachi (SEQ ID NO: 18)
- Kanpachi (SEQ ID NO: 18)
- Hiramasa (SEQ ID NO: 18)
- Hiramasa (SEQ ID NO: 18)
- Hiramasa (SEQ ID NO: 18)
- Hiramasa (SEQ ID NO: 18)
- Hiramasa (SEQ ID NO: 18)
- Buri (SEQ ID NO: 19)
- Buri (SEQ ID NO: 19)
- Buri (SEQ ID NO: 19)
- Buri (SEQ ID NO: 19)
- Buri (SEQ ID NO: 19)

METHOD FOR DISCRIMINATING SEX OF YELLOWTAIL GROUP

CROSS-REFERENCE TO RELATED APPLICATIONS

This application is a National Stage of International Application No. PCT/JP2019/005821 filed on Feb. 18, 2019, which claims priority under U.S.C. § 119 (a) to Japanese Patent Application No. JP 2018-027260 filed Feb. 19, 2018, and all of the entities of its disclosure are incorporated herein by reference.

TECHNICAL FIELD

The present invention relates to a method for identifying sex of yellowtails. More specifically, the present invention relates to a method for inspecting the sex of yellowtail using the single nucleotide polymorphism (SNP) present in the sex determining gene.

BACKGROUND ART

Yellowtail is an important aquaculture target species, which accounts for the majority of marine aquaculture production in Japan. Under the circumstances, yellowtail aquaculture relies on natural resources to collect natural seedlings and raise them up to the shipping size. For more stable aquaculture production, technological development is being carried out regarding the early introduction of artificial seedlings that do not depend on natural seedlings and the provision of superior traits to artificial seedlings.

In the production of seedlings of yellowtails, there is a demand for sex discrimination from the early stage of the pre-maturity growth stage where it is not possible to distinguish between sex from the external form. In many cases, males always sperm during maturation, sperm collection is relatively easy, and cryopreservation technology has been established. On the other hand, females can collect good quality eggs from one individual for a short period of time, and often do not ovulate due to handling during confirmation of incubation, so it is difficult to determine the timing of collecting eggs. Accordingly, for the purpose of mating, it is difficult to collect good quality eggs from a certain female parent fish. In addition, it is said that females are not suitable as commercial products for the shipment of cultured yellowtails, because the weight of females decreases in the spawning season in early spring. Therefore, if it is possible to identify males and females, there is an advantage that the number of male and female of the cultured parent fishes can be adjusted, and the shipping time can be adjusted depending on the males and females.

As a method for identifying sex of yellowtails, it has been reported that the sex determination locus of yellowtail was determined to be present between the microsatellite DNA marker loci Sequ17 and Sequ21 on the linkage group LG12, and that sex based is determined based on the difference in size of amplification products derived from the specific sequences in this microsatellite DNA marker locus Sequ21. (Patent Document 1, Non-Patent Document 1). However, there is still a considerable physical distance between this microsatellite DNA marker locus and the genomic region that determines genetic sex, and there was a risk that sex cannot be discriminated by genetic differences within the population and recombination of the genome. There was a risk of disappearing.

In addition, it is reported that male and female can be discriminated by examining the region between Sequ17 and Sequ21 of linkage group 12 in more detail, and by examining the genotype of at least one of the two SNP markers present in this region, which is a single nucleotide polymorphism. (Patent Document 2, Non-Patent Document 2). However, there is still a physical distance between these two SNP markers and the region that determines the genetic sex, and the specific verification is limited to wild yellowtail individuals. Therefore, it can be said that there is still a need for a method that enables accurate identification of male and female yellowtails.

CITATION LIST

Patent Document

Patent document 1: JP 2010-226974 A
Patent document 2: JP 2014-180233 A

Non-Patent Document

Non-Patent document 1: Aquaculture Vol. 308, Supplement 1, pp. S51-S55 (2010)
Non-Patent document 2: Marine Biotechnology Vol. 17, pp. 502-514 (2015)

SUMMARY OF INVENTION

The present inventors determined the base sequence of the sex-determining region of the Japanese yellowtail (Buri) linkage group LG12, and based on the base sequence, identified the same regions of the related species, Greater amberjack (Kanpachi) and yellow tail amberjack (Hiramasa). Furthermore, when these nucleotide sequences were compared, the 169th single nucleotide polymorphism (Squ101Chr12 666032) in the nucleotide sequence of exon 3 of the sex determination gene HSD17B1 was A/A in males, A/G or G/G in females. It was found that the genotype of the single nucleotide polymorphism or the amino acid residue corresponding thereto or its codon was used as an index to accurately identify the genetic sex of Japanese yellowtail, Greater amberjack and yellow tail amberjack. The present invention is based on this finding.

Therefore, an object of the present invention is to provide a method capable of accurately identifying the sex of yellowtails.

The present invention includes the following inventions.

(1) A method for identifying sex of yellowtails, comprising the step of identifying whether the 143rd amino acid residue in the polypeptide encoded by the yellowtail HSD17B1 gene is a glutamic acid residue or a glycine residue.

(2) The method according to (1), wherein said identification step comprises identifying in the HSD17B1 gene whether the codon corresponding to the 143rd amino acid residue of the polypeptide corresponds to a glutamic acid residue or a glycine residue.

(3) The method according to (1) or (2), wherein the polypeptide comprises the amino acid sequence set forth in SEQ ID NO: 2, 5 or 8.

(4) The method according to any one of (1) to (3), the sex of yellowtail is determined to be male when the 143rd amino acid residue of the polypeptide is only a glutamic acid residue, and the sex of the yellowtail is determined to be female when the 143rd amino acid residue of the polypeptide is only a glycine residue or when the 143rd amino acid residue of the polypeptide is the glycine residue or glutamine residue.

(5) The method according to any one of (1) to (4), wherein the identifying step is a step of identifying whether the 169th nucleotide residue in exon 3 of the HSD17B1 gene is an adenine (A) residue or a guanine (G) residue.

(6) The method according to (5), wherein the sex of the yellowtail is determined to be male when the 169th nucleotide residue in exon 3 of the HSD17B1 gene is only an adenine (A) residue, and the sex of yellowtail is determined to be female when the 169th nucleotide residue in exon 3 of the HSD17B1 gene is a guanine (G) residue or an adenine (A) residue.

(7) The method according to any one of (1) to (6), wherein the identifying step comprises amplifying a polynucleotide encoding at least a part of the HSD17B1 gene genomic sequence or a polynucleotide complementary thereto by a nucleic acid amplification method.

(8) The method according to (7), wherein the polynucleotide comprises a region containing a residue corresponding to the nucleotide residue located at 169th position of exon 3 of the HSD17B1 gene.

(9) The method according to (7) or (8), wherein the polynucleotide comprises any of the following base sequences or a part thereof:
 (i) A base sequence set forth in SEQ ID NO: 1, 4 or 7;
 (ii) A nucleotide sequence set forth in SEQ ID NO: 3, 6 or 9.

(10) The method according to any one of (1) to (9), wherein the sex discrimination is genetic sex discrimination.

(11) The method according to any one of (1) to (10), wherein the yellowtails consist of Japanese yellowtail, greater amberjack or yellowtail amberjack.

(12) A nucleic acid molecule for use in the method according to any one of (1) to (11), which comprises a nucleotide fragment that hybridizes to a polynucleotide encoding at least a part of the HSD17B1 gene genomic sequence or a polynucleotide complementary thereto and wherein the polynucleotide comprises a region containing a residue corresponding to the nucleotide residue located at the 169th position in exon 3 of the HSD17B1 gene.

(13) A primer pair for use in the method according to any one of (1) to (11), which is capable of amplifying a nucleotide region containing a residue corresponding to the nucleotide residue located at position 169 of exon 3 in the HSD17B1 gene in a polynucleotide encoding at least a part of the HSD17B1 gene genomic sequence or a polynucleotide complementary thereto.

(14) A kit for identifying sex of yellowtail comprising any one of the following reagents:
 a reagent capable of identifying whether the 143rd amino acid residue in the polypeptide encoded by the HSD17B1 gene of yellowtails is a glutamic acid residue or a glycine residue;
 a reagent capable of identifying in the HSD17B1 gene of yellowtails whether the codon corresponding to the 143rd amino acid residue of the polypeptide encoded by the gene corresponds to a glutamic acid residue or a glycine residue;
 a reagent capable of identifying whether a nucleotide residue at the 428th position of the polypeptide coding region of the HSD17B1 gene of yellowtails is an adenine (A) residue or a guanine (G) residue;
 a reagent capable of identifying whether the 169th nucleotide residue in exon 3 of the HSD17B1 gene of yellowtails is an adenine (A) residue or a guanine (G) residue.

(15) The kit for identifying the sex of yellowtails according to (14), which comprises the nucleic acid molecule according to (12) and/or the primer pair according to (13).

According to the present invention, the sex of yellowtails can be accurately identified without being affected by genetic differences within a population or recombination of genomes. Further, according to the present invention, the sex of yellowtails alive can be identified before sexual maturity. Furthermore, according to the present invention, the sex of yellowtails can be easily and quickly discriminated using the genotype of single nucleotide polymorphism or the amino acid residue corresponding thereto or its codon as an index. Since male and female can be determined at an early stage according to the present invention, it can be used particularly advantageously in adjusting the number of male and female of a parent fish to be cultured and in adjusting the shipping time depending on males or females.

BRIEF DESCRIPTION OF DRAWINGS

FIG. 1 is the FIGURE which show the result that the genotype of the 169th single nucleotide polymorphism in the nucleotide sequence of exon 3 of HSD17B1 gene was correlated with the result of sex determination by observing the external morphology of the gonad after laparotomy in each of 10 wild individuals of Japanese yellowtail, greater amberjack or yellowtail amberjack. Here, the base sequence R represents A or G, and the base sequence S represents C or G. The reference sequence indicates the location of the single nucleotide polymorphism when the nucleotide sequences derived from the individuals are compared. The downward black triangle indicates the site of the 169th nucleotide residue.

DETAILED EXPLANATION OF THE INVENTION

Method for Identifying the Sex of Yellowtail
Identification Step

The method of identifying the sex of yellowtail of the present invention is performed by determining whether the 143rd amino acid residue in the polypeptide encoded by the HSD17B1 gene of yellowtail is a glutamic acid residue or a glycine residue. It is characterized by including a step of identifying whether it is a group (hereinafter, also simply referred to as "identification step"). One nucleotide residue of the codon corresponding to the 143rd amino acid residue in the polypeptide encoded by the HSD17B1 gene is the 169th nucleotide sequence of the exon 3 found as an index for sex discrimination in yellowtail. Is a residue corresponding to the nucleotide residue of. Therefore, the 143rd amino acid residue or its codon in the polypeptide encoded by the HSD17B1 gene corresponds to the single nucleotide polymorphism of the 169th nucleotide residue in the nucleotide sequence of exon 3 and is accurate for the identification of male and female yellowtail.

The yellowtails of the present invention is a fish of the genus *Seriola*, and includes, in Japanese names, Buri (Japanese yellowtail) (scientific name: *Seriola quinqueradiata*), Hiramasa (yellowtail amberjack) (scientific name: *Seriola lalandi*), Kanpachi (greater amberjack) (scientific name: *Seriola dumerili*), Hirenagakanpachi (scientific name: *Seriola rivoliana*), Aoburi, Gando, Gandoburi, Mojaco, Mojacco, Inada, Inara, Warasa, Kozokura, Kozukura, Tsubaiso, Fukuragi, Fukurage, Wakana, Shojingo, Tsubasu, Yazu, Hamachi, Meji, Mejiro, Hanajiro, Marugo, Wakanago, Ooina, Suzuina, Ooio, Wakashi, Masagi, Hirasa, Hirasu, Hiraso, Tenkotsu, Sentoku, Agayu, Maya, and fishes in foreign names such as, (Japanese, great, greater, southern) Amberjack, (Five-ray) Yellowtail, kingfish, Almaco jack. In a preferred embodiment of the present invention, the yellowtails consist of Buri (Japanese yellowtail), Hiramasa (Yellowtail amberjack) and Kanpachi (Greater amberjack).

The HSD17B1 gene of the yellowtail of the present invention is present on the linkage group LG21, and as described above, the genotype of the single nucleotide polymorphism contained in it or the amino acid residue corresponding thereto or its codon can be used as an index of the accurate female and male discrimination of the yellowtails. Specific nucleotide sequences of the polypeptide coding region of the HSD17B1 gene used for such discrimination of male and female yellowtails of the present invention include SEQ ID NOs: 1, 4 and 7. The 428th nucleotide residue in the nucleotide sequence set forth in SEQ ID NO: 1, 4 or 7 corresponds to the 169th nucleotide residue of exon 3 of the HSD17B1 gene, which is an index for determining sex of yellowtail male and female. When the yellowtail of the present invention is Japanese amberjack, the nucleotide sequence of the polypeptide coding region of the HSD17B1 gene is preferably SEQ ID NO: 1. When the yellowtail of the present invention is Greater amberjack, the nucleotide sequence of the polypeptide coding region of the HSD17B1 gene is preferably SEQ ID NO:4. When the yellowtail of the present invention is Yellowtail amberjack, the nucleotide sequence of the polypeptide coding region of the HSD17B1 gene is preferably SEQ ID NO:7.

The amino acid sequence of the polypeptide encoded by the HSD17B1 gene of the present invention includes SEQ ID NO: 2, 5 or 8. When the yellowtail of the present invention is Japanese amberjack, the amino acid sequence of the polypeptide encoded by the HSD17B1 gene is preferably SEQ ID NO:2. When the yellowtail of the present invention is Greater amberjack, the amino acid sequence of the polypeptide encoded by the HSD17B1 gene is preferably SEQ ID NO:5. When the yellowtail of the present invention is Yellowtail amberjack, the amino acid sequence of the polypeptide encoded by the HSD17B1 gene is preferably SEQ ID NO:8.

Further, exon 3 of the HSD17B1 gene of the present invention contains a single nucleotide polymorphism that serves as an index for male and female discrimination as described above, and its nucleotide sequence includes SEQ ID NO: 3, 6 or 9. When the yellowtail of the present invention is Japanese amberjack, the nucleotide sequence of exon 3 of the HSD17B1 gene is preferably SEQ ID NO:3. When the yellowtail of the present invention is Greater amberjack, the nucleotide sequence of exon 3 of the HSD17B1 gene is preferably SEQ ID NO:6. When the yellowtail of the present invention is Yellowtail amberjack, the nucleotide sequence of exon 3 of the HSD17B1 gene is preferably SEQ ID NO:9.

In the identification step of the present invention, as described above, while the 143rd amino acid residue in the polypeptide encoded by the HSD17B1 gene may be used as an index for identifying the sex of yellowtails, the corresponding codon may be used as an index. Therefore, according to one embodiment, in the method of the present invention, the identifying step includes determining whether the codon corresponding to the 143rd amino acid residue of the polypeptide corresponds to a glutamic acid residue or a glycine residue.

From the viewpoint of more accurate discrimination of the sex of yellowtails, it is more preferable to use a the genotype of the 169th single nucleotide polymorphism (nucleotide residue) in the exon 3 of the HSD17B1 gene contained in the codon corresponding to the 143rd amino acid residue as an index. Therefore, according to a more preferred embodiment of the present invention, the above-mentioned identification step is a step of identifying whether the 169th nucleotide residue in exon 3 of the HSD17B1 gene is an adenine (A) residue or a guanine (G) residue.

Further, the 169th single nucleotide polymorphism in exon 3 of the HSD17B1 gene corresponds to the 428th single nucleotide polymorphism of the polypeptide coding region of the HSD17B1 gene. Accordingly, the genotype can be used as an index for sex discrimination in yellowtails. Therefore, according to another more preferred embodiment of the present invention, the above-mentioned identification step is a step of identifying whether the 428th nucleotide residue of the polypeptide coding region in the HSD17B1 gene is an adenine (A) residue or a guanine (G) residue.

In the present invention, a sample is collected from, for example, a part of individuals of yellowtails as the subject, such as fin (caudal fin, dorsal fin, pectoral fin, pectoral fin, hip fin), blood, a tissue in which nucleus exists such as kidney muscle. From the obtained sample, a nucleic acid sample may be produced and then used, wherein the nucleic acid sample is extracted from a nucleic acid sample such as genomic DNA or mRNA and produced by preparing cDNA from mRNA by reverse transcriptase if necessary. By using the obtained nucleic acid sample as a template, and carrying out the nucleic acid amplification method by using for example, a primer pair described later, the nucleic acid sample can be obtained for use. As the nucleic acid amplification method, for example, a normal PCR method can be used when genomic DNA or cDNA is used as a template, and an RT-PCR method, NASBA method or the like can be used when mRNA is used as a template.

As a preferred embodiment of the method of the present invention, there is provided a method comprising amplifying a polynucleotide encoding at least a part of the genomic sequence of HSD17B1 gene of yellowtails or a polynucleotide complementary thereto by a nucleic acid amplification method. In such an embodiment, the primers used in the nucleic acid amplification method and the reaction conditions for nucleic acid amplification can be appropriately selected according to the common general technical knowledge well known to those skilled in the art. Here, the polynucleotide preferably comprises any of the following base sequences or a part thereof:
  (i) the base sequence set forth in SEQ ID NO: 1, 4 or 7;
  (ii) A nucleotide sequence set forth in SEQ ID NO: 3, 6 or 9.

In a preferred embodiment of the method of the present invention, the nucleic acid amplification method can be carried out by using a pair of primers for amplification of a region containing a residue corresponding to the 169th nucleotide residue of exon 3 of HSD17B1 gene of yellowtails. Two primers constituting such a primer pair can be appropriately designed by those skilled in the art based on the base sequence of the region to be amplified. For example, one primer of the primer pair may have the base sequence of the 5'end portion in the base sequence of the amplification target region, and the other primer may have the base sequence of the 5'end portion of the base sequence of the complementary strand of the amplification target region.

In the method of the present invention, when the nucleic acid amplification method is used, the chain length of the primer is 15 to 100 nucleotides, more preferably at least 17 nucleotides, further preferably at least 18 nucleotides, further preferably 18 to 50 nucleotides, still more preferably 18 to 40 nucleotides. A primer having such a chain length is particularly preferable for carrying out the nucleic acid amplification method using a nucleic acid sample containing contaminants.

The analysis of the base sequence of the amplification product obtained by the nucleic acid amplification method can be easily performed by, for example, the direct sequencing method using a sequencing primer. Such methods are well known in the art and can be carried out, for example, using commercially available kits.

When carrying out the above-mentioned identification step by the above-mentioned nucleic acid amplification method and direct sequence method, nucleic acid amplification may be performed using for example, a primer having the following sequence:

```
Forward:
                                  (SEQ ID NO: 10)
5'-ATGCCACAATGAGGAACCTG-3';

Reverse:
                                  (SEQ ID NO: 11)
5'-ACTCAGGGTGCAAGATGCAG-3',
``` and the direct sequencing method can be performed using these primers as sequence primers. Alternatively, another primer may be used as the sequence primer.

In the method of the present invention, when the nucleic acid amplification method is used, the primers can be designed so that the allele-specific PCR method can be carried out. Specifically, one of the primers can be designed so as to be able to pair with a single nucleotide polymorphism at the 169th nucleotide residue in the nucleotide sequence of exon 3 of the HSD17B1 gene of yellowtail (either a guanine (G) residue or an adenine (A) residue), and the other can be designed so as to be able to pair with the region containing no single nucleotide polymorphism at the 169th nucleotide residue. In the case where the nucleic acid amplification method is carried out using the primer pair designed in this way, an amplification product is obtained when the single nucleotide polymorphism is present in the nucleic acid sample, and no amplification product is obtained when the single nucleotide polymorphism is not present. Therefore, in this case, the presence or absence of the single nucleotide polymorphism can be determined by detecting the presence or absence of the amplification product.

In another preferred embodiment of the method of the present invention, a method utilizing restriction fragment length polymorphism (RFLP), for example, the PCR-RFLP method can be used when the recognition sequence by a specific restriction enzyme is lost or generated by the above-mentioned single nucleotide polymorphism. Such a method can be carried out by, for example, using a primer pair that amplifies the region including the restriction enzyme recognition sequence in the above-mentioned nucleic acid amplification method, digesting the obtained amplified fragment with this restriction enzyme, and then examining the number of fragments and their chain length.

Such methods are well known in the art, and those skilled in the art can appropriately set suitable restriction enzymes, primers, amplification reaction conditions, restriction enzyme reaction conditions, and the like.

When the above-mentioned identification step is carried out by the above-mentioned PCR-RFLP method, for example, a primer having the following sequence:

```
forward:
                                  (SEQ ID NO: 12)
5'-TACCAGAGATGAAGGCTCAG-3';

reverse:
                                  (SEQ ID NO: 13)
5'-CATTTGCTTGTCTCACCGTG-3'
``` can be used to perform nucleic acid amplification. Further, it is possible to count the number of DNA fragments by cleaving the 82 bp DNA fragment obtained by this amplification with a restriction enzyme BsaWI that specifically recognizes and cleaves the nucleotide sequence wherein an adenine (A) residue is substituted with the (G) residue at the 169th nucleotide residue in the nucleotide sequence of exon 3 of the HSD17B1 gene of yellowtail.

In another preferable embodiment of the method of the present invention, the above-mentioned identification step can be carried out by a hybridization method using a probe. Such a probe can be appropriately designed by those skilled in the art based on the base sequence of the region. Therefore, according to the present invention, there is provided a method for identifying sex of yellow tails, comprising a step of performing hybridization between the probe and a nucleic acid sample as an analyte derived from an individual of the yellowtails, and then detecting the presence of a hybridization complex. The presence of the hybridization complex indicates the presence of the single nucleotide polymorphism in the sex determining gene HSD17B1 of yellowtails. This method using the hybridization method can also be applied to a nucleic acid sample that is an amplification product obtained by the method using the nucleic acid amplification method described above.

When used in the hybridization method, the chain length of the probe is 15 to 100 nucleotides, more preferably at least 17 nucleotides, still more preferably at least 18 nucleotides, further preferably 18 to 50 nucleotides, still more preferably 18 to 40 nucleotides. A probe having such a chain length is particularly preferable for carrying out the hybridization method using a nucleic acid sample containing impurities.

In identifying the genetic sex of yellowtails by the hybridization method, the presence or absence of hybridization between the nucleic acid sample and the above-mentioned probe detected under stringent conditions enables to detect the presence of a single nucleotide polymorphism at the 169th nucleotide residue. In the method of the present invention, "stringent conditions" means, as conditions for hybridization, "5×SSPE, 5×Denhardt's solution, 0.5% sodium dodecyl sulfate (SDS), 50% formamide, 200 µg/mL salmon sperm DNA, 42° C. overnight", and conditions for washing are "0.5×SSC, 0.1% SDS, 42° C." The "more stringent conditions" are the conditions for hybridization, which are "5×SSPE, 5×Denhardt's solution, 0.5% SDS, 50% formamide, 200 µg/mL salmon sperm DNA, 42° C. overnight" and the conditions for cleaning are "0.2×SSC, 0.1% SDS, 65° C."

If necessary, the nucleic acid sample may be subjected to restriction enzyme treatment or the like to have a length suitable for hybridization. As the hybridization method and the method for detecting a single nucleotide polymorphism thereby, any method known in the art may be used. For example, techniques such as southern hybridization and colony hybridization can be used. For details of these methods, see, for example, J. Sambrook, E. F. Frisch, T. Maniatis; Molecular Cloning 2nd edition, Cold Spring Harbor Laboratory (1989).

In the method of the present invention, in the case of detecting a single nucleotide polymorphism by a hybridization method, the presence or absence of hybridization may be detected by preparing a DNA chip wherein the above-mentioned probe is immobilized on a substrate, contacting the DNA chip and a nucleic acid sample derived from an individual of yellowtails as a test subject under hybridization conditions.

Therefore, according to the present invention, there is provided a DNA chip capable of detecting a single nucleotide polymorphism at the 169th nucleotide residue, wherein the above-mentioned probe is immobilized on a substrate, and further, a method of identifying the genetic sex of yellowtails comprising the step of detecting the single nucleotide polymorphisms using this DNA chip. In the present invention, the chain length of the probe bound to the substrate is not particularly limited, but is preferably 15 to 100 nucleotides, more preferably 15 to 50 nucleotides, and further preferably 17 to 25 nucleotides. Techniques for detecting single nucleotide polymorphisms using such a DNA chip are well known in the art (post-sequence genomic science, Volume 1, "SNP gene polymorphism strategy", Kenichi Matsubara, Yoshiyuki Sakaki, Nakayama Bookstore, p 128-135, 2000), a person skilled in the art can prepare an appropriate DNA chip using the above-mentioned probe and detect the single nucleotide polymorphism using this DNA chip.

Further, as another aspect of the method of the present invention, single nucleotide polymorphisms in residues the 169th nucleotide can be detected by using a primer extension method such as SNaPshot™ method or Pyrosequencing method, or a Genotyping method (typing method) such as TaqMan PCR method. These techniques are known to those skilled in the art, and the operating procedure thereof and the specific base sequences of the primers and/or probes to be used can be easily determined by those skilled in the art. However, the method is not limited to these, and any method can be used as long as it can detect single nucleotide polymorphisms in a gene.

Judgment Step

In the present invention, as shown in Examples described later, the sex of yellowtails can be determined by the above-described nucleic acid analysis using as an index the 143rd amino acid residue in the polypeptide encoded by the HSD17B1 gene or its corresponding codon, or the polymorphic genotype of the 169th single base in exon 3 of the HSD17B1 gene or the corresponding polymorphic genotype of the 428th single nucleotide polymorphism in the polypeptide coding region of the HSD17B1 gene.

According to one aspect of the present invention, the sex of yellowtails can be determined to be male when the 143rd amino acid residue in the polypeptide encoded by the HSD17B1 gene is used as an index for identifying sex of yellowtails and the 143rd amino acid residue in the polypeptide encoded by the HSD17B1 gene is only glutamic acid residues. Further, the sex of the yellowtail can be determined to be female when the 143rd amino acid residue of the above polypeptide is only a glycine residue, or is a glycine residue or a glutamine residue.

Further, according to another preferred embodiment, the sex of yellowtail can be determined to be male when the genotype of the 169th single nucleotide polymorphism in exon 3 of the HSD17B1 gene is used as an index for identifying the sex of yellowtails and the 169th nucleotide residue in the exon 3 of the exon 3 of the HSD17B1 gene is only an adenine (A) residue. Further, the sex of yellowtail can be determined to be female when the 169th (or the 428th position of the corresponding polypeptide coding region) nucleotide residue in the exon 3 is only a guanine (G) residue, or a guanine (G) residue or an adenine (A) residue.

According to still another preferred embodiment, the sex of yellowtails can be determined to be male when the genotype of the 428th single nucleotide polymorphism in the polypeptide coding region of the HSD17B1 gene is used as an index of the sex of yellowtails and the 428th position of the polypeptide coding region of the HSD17B1 gene is only an adenine (A) residue. Further, the sex of yellowtails can be determined to be a female when the 428th nucleotide residue of the polypeptide coding region is only a guanine (G) residue, or is a guanine (G) residue or an adenine (A) residue.

Nucleic Acid Molecule/Primer Pair

As another aspect of the present invention, a nucleic acid molecule for use in the method of the present invention is provided. A preferred nucleic acid molecule of the present invention comprises a nucleotide fragment that hybridizes to a polynucleotide encoding at least a part of the HSD17B1 gene genomic sequence of yellowtails or a polynucleotide complementary thereto, and the polynucleotide comprises a region containing a residue corresponding to the nucleotide residue located at the 169th position in exon 3 of the HSD17B1 gene. In a preferred embodiment of the present invention, the nucleic acid molecule of the present invention can be used as a probe in a hybridization method. A nucleic acid molecule used as such a probe can be appropriately designed by those skilled in the art based on the base sequence of the region. When used as a probe in a hybridization method, the chain length of the nucleic acid molecule is 15 to 100 nucleotides, more preferably at least 17 nucleotides, still more preferably at least 18 nucleotides, still more preferably 18 to 50 nucleotides, still more preferably 18 to to 40 nucleotides. A nucleic acid molecule as a probe having such a chain length is particularly preferable for carrying out the hybridization method using a nucleic acid sample containing impurities.

As another aspect of the present invention, a primer pair for use in the method of the present invention is provided. A preferred primer pair of the present invention is a polynucleotide encoding at least a part of the HSD17B1 gene genomic sequence of yellowtails or a polynucleotide complementary thereto, which is located at the 169th nucleotide of exon 3 of HSD17B1 gene of yellowtails. A nucleotide region containing a residue corresponding to a residue can be amplified in a nucleic acid amplification method. A primer pair for use in such a nucleic acid amplification method can be appropriately designed by those skilled in the art based on the base sequence of the region. When using the nucleic acid amplification method, the chain length of the primer is set to 15 to 100 nucleotides, more preferably at least 17 nucleotides, further preferably at least 18 nucleotides, further preferably 18 to 50 nucleotides, still more preferably 18 to 40 nucleotides. It A primer having such a chain length is particularly preferable for carrying out the nucleic acid amplification method using a nucleic acid sample containing contaminants.

Reagent/Kit

In the present invention, the 143rd amino acid residue in the polypeptide encoded by the HSD17B1 gene of yellowtail or its corresponding codon, or the 169th single nucleotide polymorphism in exon 3 of the HSD17B1 gene or this The reagents necessary for carrying out the method for discriminating the sex of yellowtail using the genotype of the 428th single nucleotide polymorphism of the polypeptide coding region of the HSD17B1 gene corresponding to the above can be put together into a kit. Therefore, according to one aspect, the kit of the present invention can identify whether the 143rd amino acid residue in the polypeptide encoded by the HSD17B1 gene of yellowtail is a glutamic acid residue or a glycine residue. Reagent: A reagent capable of identifying whether the codon corresponding to the 143rd amino acid residue of the polypeptide encoded by the HSD17B1 gene of yellowtail corresponds to a glutamic acid residue or a glycine residue; Reagent for identifying whether the 428th nucleotide residue of the polypeptide coding region of the HSD17B1 gene is an adenine (A) residue or a guanine (G) residue; Exon 3 of the HSD17B1 gene of yellowtail And a reagent capable of identifying whether the 169th nucleotide residue in is adenine (A) residue or guanine (G) residue.

The kit of the present invention may comprise the nucleic acid molecule of the present invention and/or the primer pair of the present invention as a reagent.

Further, the kit of the present invention is an indicator of the 143rd amino acid residue of the polypeptide encoded by the HSD17B1 gene (whether it is a glutamic acid residue or a glycine residue) in the protein expressed by the HSD17B1 gene of yellowtail. An antibody capable of discriminating the above may be included as a reagent, and the present invention also includes such an embodiment.

Use as a marker for distinguishing sex of yellowtail/marker In the present invention, as long as the above-mentioned single nucleotide polymorphism or amino acid mutation corresponding thereto is included, nucleotides, polypeptides or HSD17B1 gene derived from yellowtail These fragments can be used as a marker for identifying the sex of yellowtail.

Therefore, according to another aspect of the present invention, there is provided a marker for sex identification of yellowtail, which comprises the polypeptide represented by the amino acid sequence represented by SEQ ID NO: 2, 5 or 8 or a peptide fragment thereof. According to yet another aspect, there is provided use of the polypeptide represented by the amino acid sequence represented by SEQ ID NO: 2, 5 or 8 or a peptide fragment thereof as a marker for identifying sex of yellowtail. In any of the above embodiments, the peptide fragment preferably comprises a residue corresponding to the 143rd amino acid residue in the amino acid sequence represented by SEQ ID NO: 2, 5 or 8.

According to another aspect, there is provided a sex identification marker for yellowtail, which comprises the polynucleotide represented by the following nucleotide sequence (i) or (ii) or a nucleotide fragment thereof: (i) the nucleotide sequence represented by SEQ ID NO: 1, 4 or 7; (ii) the nucleotide sequence represented by SEQ ID NO: 3, 6 or 9. According to still another aspect, there is provided use of the polynucleotide represented by the nucleotide sequence of (i) or (ii) or a nucleotide fragment thereof as a marker for identifying the sex of yellowtail. In any of the above embodiments, the nucleotide fragment preferably comprises a residue corresponding to the 428th nucleotide residue in the base sequence represented by SEQ ID NO: 1, 4 or 7. Further, in any of the above embodiments, the nucleotide fragment preferably comprises a residue corresponding to the 169th nucleotide residue in the nucleotide sequence represented by SEQ ID NO: 3, 6 or 9.

Those skilled in the art can suitably use the nucleic acid molecule, the pair, the kit, the marker for identifying sex of yellowtail and the use as a marker according to the method for identifying yellowtail of the present invention.

The present invention will be described based on the following examples, but the present invention is not limited to these examples.

Example 1: Identification of a Sex Determining Gene Common to Three Species of Yellowtails and Single Nucleotide Polymorphisms that Govern Sex Determination in the Sex Determining Gene BAC (bacterial artificial chromosomal) clones which has the genome sequence of the sex-determining region of the yellowtail linkage group LG12 were screened and the highly accurate nucleotide sequence of the clones was determined. Next, based on the nucleotide sequence of the sex-determining region of Japanese amberjack, the genomic DNA of the sex-determining regions of the closely related species Greater amberjack and Yellowtail amberjack were obtained using Roche's exome enrichment kit "SeqCapEZ (ver.3)." Then, the base sequences of the sex determining regions of Greater amberjack and Yellowtail amberjack were determined. Using the determined nucleotide sequence of the sex determining region as a reference sequence, a correlation analysis between single nucleotide polymorphisms in the sex determining region and sex was performed to identify the sex determining gene HSD17B1 common to the three species. The nucleotide sequence of the polypeptide coding region of the Japanese amberjack's HSD17B1 gene is shown in SEQ ID NO:1, and the amino acid sequence of the polypeptide encoded by the Japanese amberjack's HSD17B1 gene is shown in SEQ ID NO:2. The nucleotide sequence of the polypeptide coding region of the Greater amberjack's HSD17B1 gene is shown in SEQ ID NO:4, and the amino acid sequence of the polypeptide encoded by the Greater amberjack's HSD17B1 gene is shown in SEQ ID NO:5. The nucleotide sequence of the polypeptide coding region of the Yellowtail amberjack's HSD17B1 gene is shown in SEQ ID NO:7, and the amino acid sequence of the polypeptide encoded by the Yellowtail amberjack's HSD17B1 gene is shown in SEQ ID NO:8. In addition, sex determination as a phenotype of Japanese amberjack, Greater amberjack, and Yellowtail amberjack was performed by observing the external morphology of the gonad after laparotomy.

Comparing the nucleotide sequences of the three sex determining genes HSD17B1 revealed that the genotype of the 169th nucleotide residue in the nucleotide sequence of exon 3, which is a novel single nucleotide polymorphism (SNP), was A/G or G/G in females, and A/A in males. Such a single nucleotide polymorphism is also referred to as Squ101Chr12 666032. Here, the nucleotide sequence of exon 3 of the Japanese amberjack's HSD17B1 gene is shown in SEQ ID NO:3. The nucleotide sequence of exon 3 of the Greater amberjack's HSD17B1 gene is shown in SEQ ID NO:6. In addition, the nucleotide sequence of exon 3 of the Yellowtail amberjack's HSD17B1 gene is shown in SEQ ID NO:9. The HSD17B1 gene encodes 17β-hydroxysteroid dehydrogenase subtype 1, which is a steroid-metabolizing enzyme. Recombinant proteins were prepared by expressing in *Escherichia coli* the polypeptides encoded by the Japanese amberjack's HSD17B1 gene when the genotype of the 169th nucleotide residue in the exon 3 nucleotide sequence is A or G, respectively. Next, According to the enzyme assay method described in Ferdinand H., et al. J. Mol. Biol. vol. 399, pp. 255-267 (2010), the enzymatic reaction products of each proteins were obtained. The enzyme reaction products were quantified by LC/MS/MS (liquid chromatography/ mass spectrometry) to determine the steroid metabolism activity (17β-hydroxysteroid dehydrogenase activity (estron-estradiol conversion activity and androstenedione-testosterone conversion activity)) was measured. As a result, the protein having a genotype of G has a higher enzyme activity than the protein having a genotype of A. And, It became clear that the individual differentiates into a female when at least one of the genotypes is G.

The yellowtails has a ZZ/ZW type sex determination pattern and differentiate into a female when it has a W chromosome. In the Z-type sex determining gene located on the Z chromosome, the genotype of the 169th nucleotide residue in the nucleotide sequence of exon 3 is A, and the amino acid encoding this region is glutamic acid. On the other hand, in the sex-determining gene W type located on the W chromosome, the genotype of the 169th nucleotide residue in the nucleotide sequence of exon 3 is G, and the encoded amino acid is glycine.

Based on the above findings, it can be determined to be male (ZZ type) when genotype at the 169th nucleotide residue of the nucleotide sequence of exon 3 of the HSD17B1 gene of yellowtails (corresponding to the 428th nucleotide residue of the nucleotide sequence of the polypeptide coding region of HSD17B1 gene of yellowtails) is A/A (corresponding 143rd amino acid residue is glutamic acid/glutamic acid) and it can be determined to be female (ZW type or WW type) when the genotype is A/G or G/G (corresponding 143rd amino acid residue is glutamic acid/ glycine or glycine/glycine).

Example 2: Discrimination of Genetic Sex of Yellowtails by Nucleic Acid Amplification Method and Direct Sequence Method Regarding Japanese amberjack, Greater amberjack and Yellowtail amberjack, 10 wild animals of were rescpectively laparotomized and the external morphology of the gonads was observed to determine gender as the phenotype. Caudal fins were collected from these yellowtails and DNA was extracted. Next, the peripheral region containing the single nucleotide polymorphism was amplified by the PCR method. As the PCR primers, polynucleotides having the base sequences ATGCCACAATGAGGAACCTG (SEQ ID NO: 10) and ACTCAGGGTGCAAGATGCAG (SEQ ID NO: 11) were used. The PCR reaction solution prepared in a volume of 10 μL containing 1 pmol of primer, 0.2 mM of each dNTPs, 1×ExTaqBuffer, 0.25U Extaq DNA polymerase (Takara Bio Inc.), and 50 ng of sample DNA was used. The PCR reaction was carried out under conditions of 95° C. for 3 minutes, (95° C. for 30 seconds, 53° C. for 30 seconds, 72° C. for 1 minute)×30 cycles, and 72° C. for 5 minutes. Next, the PCR amplification product was purified (removal of excess primer by enzymatic reaction) using the illustra ExoStar kit (manufactured by GE Healthcare). Then, the nucleotide sequence of the PCR product was determined by the Sanger method, and the genotype of the SNP was identified. For the sequencing primer, a polynucleotide having the base sequence ATGCCACAATGAGGAACCTG (SEQ ID NO: 10) was used.

The results are shown in FIG. 1. Regarding females, in 14 out of 15 samples, the genotype of the nucleotide residue of the single nucleotide polymorphism was G/A heterozygous, and in 1 sample, G/G homozygous. On the other hand, males were homozygous for A/A in all 15 samples.

Example 3: Identification of Genetic Sex of Yellowtails by PCR-RFLP Method

Caudal fin was collected from yellowtails and DNA was extracted. Next, the peripheral region including the SNP was amplified by the PCR method. As the PCR primers, the polynucleotides having the base sequences TACCAGAGATGAAGGCTCAG (SEQ ID NO: 12) and CATTTGCTTGTCTCACCGTG (SEQ ID NO: 13) were used. The PCR reaction solution prepared in a volume of 10 μL containing 1 pmol of primer, 0.2 mM of each dNTPs, 1×ExTaq Buffer, 0.25U Extaq DNA polymerase (Takara Bio Inc.), and 10 ng of sample DNA was used. The PCR reaction was carried out under the conditions of 95° C. for 3 minutes, (95° C. for 30 seconds, 53° C. for 30 seconds, 72° C. for 30 seconds)×30 cycles and 72° C. for 1 minute. Next, the PCR product was treated by a restriction enzyme BsaWI (New England Biolabs) that specifically recognizes and cleaves the W-type single nucleotide polymorphism (the nucleotide sequence at the 169th nucleotide residue of the nucleotide sequence of the sex determination gene HSD17B1 exon 3 is G). The reaction conditions were 60° C. for 30 minutes. The reaction solution prepared to have a solution volume of 10 μL containing 1 U restriction enzyme, 1×CutSmartBuffer, and 3 μL of PCR product was used. After that, MultiNA electrophoresis (manufactured by Shimadzu) was performed using the DNA-500 kit to visualize the mobility of the cleaved DNA fragment. 82 bp DNA fragment was amplified by PCR. Since the restriction enzyme BsaWI specifically recognizes and cleaves W-type SNPs, one DNA band for ZZ (male), three DNA bands for ZW (female), and two DNA bands for WW (female) were observed.

The invention claimed is:

1. A method for identifying sex of at least one yellowtail, comprising the steps of:
   identifying whether the 169th nucleotide residue in exon 3 of HSD17B1 gene of the at least one yellowtail is an adenine (A) residue or a guanine (G) residue,
   determining the sex of the at least one yellowtail based on the result of the identifying step, and
   separating the at least one yellowtail into male or female based on the result of the determining step and culturing the male and female yellowtails separately,
   wherein the at least one yellowtail is at least one selected from the group consisting of Japanese amberjack, Greater amberjack and Yellowtail amberjack,
   wherein the exon 3 of the HSD17B1 gene of Japanese amberjack is set forth in SEQ ID NO: 3,
   wherein the exon 3 of the HSD17B1 gene of Greater amberjack is set forth in SEQ ID NO: 6, wherein the exon 3 of the HSD17B1 gene of Yellowtail amberjack is set forth in SEQ ID NO: 9, wherein the sex of the yellowtail is determined to be male when the genotype at the 169th nucleotide residue in the exon 3 of the HSD17B1 gene is an A/A, and wherein the sex of yellowtail is determined to be female when the genotype at the 169th nucleotide residue in the exon 3 of the HSD17B1 gene is a G/G or an A/G.

2. The method according to claim 1, wherein the identifying step comprises amplifying a polynucleotide encoding at least a region of the HSD17B1 gene genomic sequence, the region containing the nucleotide residue located at 169th position of exon 3 of the HSD17B1 gene, or a polynucleotide complementary thereto by a nucleic acid amplification method.

3. The method according to claim 2, wherein the nucleic acid amplification method is conducted by using a primer pair each having a nucleotide sequence comprising SEQ ID NOs: 10 and 11 or a primer pair each having a nucleotide sequence set forth in SEQ ID NOs: 14 and 15.

* * * * *

SEQUENCE LISTING

```
<160> NUMBER OF SEQ ID NOS: 19

<210> SEQ ID NO 1
<211> LENGTH: 873
<212> TYPE: DNA
<213> ORGANISM: Seriola quinqueradiata
<220> FEATURE:
<221> NAME/KEY: CDS
<222> LOCATION: (1)..(873)
<223> OTHER INFORMATION: r=a or g, s=c or g

<400> SEQUENCE: 1
```

```
atg gac aag aag gtg gtg ctg atc aca ggc tgc tcc tcg gga atc ggc       48
Met Asp Lys Lys Val Val Leu Ile Thr Gly Cys Ser Ser Gly Ile Gly
1               5                   10                  15 ctc agc ctg gct gtc cgt ctg gca tct gac cct gaa aaa aca ttc aaa       96
Leu Ser Leu Ala Val Arg Leu Ala Ser Asp Pro Glu Lys Thr Phe Lys
                20                  25                  30 gtc tat gcc aca atg agg aac ctg gcc aag aaa gag cgt ctt tta gag      144
Val Tyr Ala Thr Met Arg Asn Leu Ala Lys Lys Glu Arg Leu Leu Glu
            35                  40                  45 tgt gtg aaa ggc ctg cac aaa gac acc ttg gac att ctc caa atg gat      192
Cys Val Lys Gly Leu His Lys Asp Thr Leu Asp Ile Leu Gln Met Asp
        50                  55                  60 gtg acg gac cgg cag tca att ctg gat gcg agg gac agg gtt gtg gag      240
Val Thr Asp Arg Gln Ser Ile Leu Asp Ala Arg Asp Arg Val Val Glu
65              70                  75                  80 aaa cga ctg gac att ctg gtg tgt aat gct ggt gtg ggt ttg atg ggg      288
Lys Arg Leu Asp Ile Leu Val Cys Asn Ala Gly Val Gly Leu Met Gly
                85                  90                  95 ccc ctg gag ctg cag tcc tcg gac tcg atg agg caa att ttg gag gtc      336
Pro Leu Glu Leu Gln Ser Ser Asp Ser Met Arg Gln Ile Leu Glu Val
            100                 105                 110 aac atc tta ggt acc atc cag acc atc cag gct ttc cta cca gag atg      384
Asn Ile Leu Gly Thr Ile Gln Thr Ile Gln Ala Phe Leu Pro Glu Met
        115                 120                 125 aag gct cag agc cag ggc cgc att ctg gtc acr ggs agc acc gra ggg      432
Lys Ala Gln Ser Gln Gly Arg Ile Leu Val Xaa Xaa Ser Thr Xaa Gly
    130                 135                 140 ctt cac ggt ctc cct ttt aat gag gtg tac tgt gcc agt aaa ttt gca      480
Leu His Gly Leu Pro Phe Asn Glu Val Tyr Cys Ala Ser Lys Phe Ala
145                 150                 155                 160 ata gag gga gca tgt gag agt ttg gcc gtc ctc ctg caa aac ttc aat      528
Ile Glu Gly Ala Cys Glu Ser Leu Ala Val Leu Leu Gln Asn Phe Asn
                165                 170                 175 atc crt gtc agt ctc att gag tgt ggt cca gtc aac aca gac ttc ctg      576
Ile Xaa Val Ser Leu Ile Glu Cys Gly Pro Val Asn Thr Asp Phe Leu
            180                 185                 190 gty aac atg cag aag gcg gag ctt ggg aat act tct ctc caa cag gtt      624
Xaa Asn Met Gln Lys Ala Glu Leu Gly Asn Thr Ser Leu Gln Gln Val
        195                 200                 205 gat acc aag aca gtc agc ctc tat gaa aaa tac ctg cag cac tgt gac      672
Asp Thr Lys Thr Val Ser Leu Tyr Glu Lys Tyr Leu Gln His Cys Asp
    210                 215                 220 tct gtt ttc caa aac gca gca cag gac act gag gac att gta aag gta      720
Ser Val Phe Gln Asn Ala Ala Gln Asp Thr Glu Asp Ile Val Lys Val
225                 230                 235                 240 ttt cta gat gcc atc cag tca ccc agt ccc acg ttc aga tat ttc acc      768
Phe Leu Asp Ala Ile Gln Ser Pro Ser Pro Thr Phe Arg Tyr Phe Thr
                245                 250                 255 agt ggt ggt rtt cca cct cta acc caa ctg aag ata aca gag cca gat      816
Ser Gly Gly Xaa Pro Pro Leu Thr Gln Leu Lys Ile Thr Glu Pro Asp
            260                 265                 270 ggc tca cag tgc atc cgt gct atg agc aaa ata atc ttc tca gtt gag      864
Gly Ser Gln Cys Ile Arg Ala Met Ser Lys Ile Ile Phe Ser Val Glu
        275                 280                 285 gaa caa taa                                                          873
Glu Gln
    290
```

<210> SEQ ID NO 2
<211> LENGTH: 290

```
<212> TYPE: PRT
<213> ORGANISM: Seriola quinqueradiata
<220> FEATURE:
<221> NAME/KEY: misc_feature
<222> LOCATION: (139)..(139)
<223> OTHER INFORMATION: The 'Xaa' at location 139 stands for Thr.
<220> FEATURE:
<221> NAME/KEY: misc_feature
<222> LOCATION: (140)..(140)
<223> OTHER INFORMATION: The 'Xaa' at location 140 stands for Gly.
<220> FEATURE:
<221> NAME/KEY: misc_feature
<222> LOCATION: (143)..(143)
<223> OTHER INFORMATION: The 'Xaa' at location 143 stands for Gly, or
      Glu.
<220> FEATURE:
<221> NAME/KEY: misc_feature
<222> LOCATION: (178)..(178)
<223> OTHER INFORMATION: The 'Xaa' at location 178 stands for Arg, or
      His.
<220> FEATURE:
<221> NAME/KEY: misc_feature
<222> LOCATION: (193)..(193)
<223> OTHER INFORMATION: The 'Xaa' at location 193 stands for Val.
<220> FEATURE:
<221> NAME/KEY: misc_feature
<222> LOCATION: (260)..(260)
<223> OTHER INFORMATION: The 'Xaa' at location 260 stands for Val, or
      Ile.

<400> SEQUENCE: 2

Met Asp Lys Lys Val Val Leu Ile Thr Gly Cys Ser Ser Gly Ile Gly
1               5                   10                  15

Leu Ser Leu Ala Val Arg Leu Ala Ser Asp Pro Glu Lys Thr Phe Lys
            20                  25                  30

Val Tyr Ala Thr Met Arg Asn Leu Ala Lys Lys Glu Arg Leu Leu Glu
        35                  40                  45

Cys Val Lys Gly Leu His Lys Asp Thr Leu Asp Ile Leu Gln Met Asp
    50                  55                  60

Val Thr Asp Arg Gln Ser Ile Leu Asp Ala Arg Asp Arg Val Val Glu
65                  70                  75                  80

Lys Arg Leu Asp Ile Leu Val Cys Asn Ala Gly Val Gly Leu Met Gly
                85                  90                  95

Pro Leu Glu Leu Gln Ser Ser Asp Ser Met Arg Gln Ile Leu Glu Val
            100                 105                 110

Asn Ile Leu Gly Thr Ile Gln Thr Ile Gln Ala Phe Leu Pro Glu Met
        115                 120                 125

Lys Ala Gln Ser Gln Gly Arg Ile Leu Val Xaa Xaa Ser Thr Xaa Gly
    130                 135                 140

Leu His Gly Leu Pro Phe Asn Glu Val Tyr Cys Ala Ser Lys Phe Ala
145                 150                 155                 160

Ile Glu Gly Ala Cys Glu Ser Leu Ala Val Leu Leu Gln Asn Phe Asn
                165                 170                 175

Ile Xaa Val Ser Leu Ile Glu Cys Gly Pro Val Asn Thr Asp Phe Leu
            180                 185                 190

Xaa Asn Met Gln Lys Ala Glu Leu Gly Asn Thr Ser Leu Gln Gln Val
        195                 200                 205

Asp Thr Lys Thr Val Ser Leu Tyr Glu Lys Tyr Leu Gln His Cys Asp
    210                 215                 220

Ser Val Phe Gln Asn Ala Ala Gln Asp Thr Glu Asp Ile Val Lys Val
225                 230                 235                 240

Phe Leu Asp Ala Ile Gln Ser Pro Ser Pro Thr Phe Arg Tyr Phe Thr
                245                 250                 255
```

```
Ser Gly Gly Xaa Pro Pro Leu Thr Gln Leu Lys Ile Thr Glu Pro Asp
            260                 265                 270

Gly Ser Gln Cys Ile Arg Ala Met Ser Lys Ile Ile Phe Ser Val Glu
        275                 280                 285

Glu Gln
    290

<210> SEQ ID NO 3
<211> LENGTH: 180
<212> TYPE: DNA
<213> ORGANISM: Seriola quinqueradiata
<220> FEATURE:
<221> NAME/KEY: exon
<222> LOCATION: (1)..(180)
<223> OTHER INFORMATION: r=a or g, s=c or g

<400> SEQUENCE: 3 tgt gta atg ctg gtg tgg gtt tga tgg ggc ccc tgg agc tgc agt cct      48
Cys Val Met Leu Val Trp Val     Trp Gly Pro Trp Ser Cys Ser Pro
1               5                       10                  15 cgg act cga tga ggc aaa ttt tgg agg tca aca tct tag gta cca tcc      96
Arg Thr Arg     Gly Lys Phe Trp Arg Ser Thr Ser     Val Pro Ser
                    20                  25 aga cca tcc agg ctt tcc tac cag aga tga agg ctc aga gcc agg gcc    144
Arg Pro Ser Arg Leu Ser Tyr Gln Arg     Arg Leu Arg Ala Arg Ala
30                  35                      40 gca ttc tgg tca crg gsa gca ccg rag ggc ttc acg                      180
Ala Phe Trp Ser Xaa Xaa Ala Pro Xaa Gly Phe Thr
45                  50                  55

<210> SEQ ID NO 4
<211> LENGTH: 873
<212> TYPE: DNA
<213> ORGANISM: Seriola dumerili
<220> FEATURE:
<221> NAME/KEY: CDS
<222> LOCATION: (1)..(873)
<223> OTHER INFORMATION: r=a or g, s=c or g

<400> SEQUENCE: 4 atg gac aag aag gtg gtg ctg atc aca ggc tgc tcc tcg gga atc ggt      48
Met Asp Lys Lys Val Val Leu Ile Thr Gly Cys Ser Ser Gly Ile Gly
1               5                   10                  15 ctc agc ctg gct gtc cgt ctg gca tct gac cct gaa aaa aca ttc aaa      96
Leu Ser Leu Ala Val Arg Leu Ala Ser Asp Pro Glu Lys Thr Phe Lys
            20                  25                  30 gtc tat gcc aca atg agg aac ctg gcc aag aaa gag cgc ctt tta gag    144
Val Tyr Ala Thr Met Arg Asn Leu Ala Lys Lys Glu Arg Leu Leu Glu
        35                  40                  45 tgt gtg aaa ggc ctg cac aaa gac acc ttg gac att ctc caa atg gat    192
Cys Val Lys Gly Leu His Lys Asp Thr Leu Asp Ile Leu Gln Met Asp
    50                  55                  60 gtg acg gac cgg cag tca att ctg gat gcg agg gac agg gtt gtg gag    240
Val Thr Asp Arg Gln Ser Ile Leu Asp Ala Arg Asp Arg Val Val Glu
65                  70                  75                  80 aaa cga ctg gac att ctg gtg tgt aat gct ggt gtg ggt ttg atg ggg    288
Lys Arg Leu Asp Ile Leu Val Cys Asn Ala Gly Val Gly Leu Met Gly
                85                  90                  95 ccc ctg gag ctg cag tcc tcg gac tcg atg agg caa aty ttg gag gtc    336
Pro Leu Glu Leu Gln Ser Ser Asp Ser Met Arg Gln Xaa Leu Glu Val
            100                 105                 110 aac atc tta ggt acc atc cag acc atc cag gct ttc cta cca gag atg    384
Asn Ile Leu Gly Thr Ile Gln Thr Ile Gln Ala Phe Leu Pro Glu Met
```

```
Asn Ile Leu Gly Thr Ile Gln Thr Ile Gln Ala Phe Leu Pro Glu Met
            115                 120                 125 aag gct cag agc cag ggc cgc att ctg gtc acg ggc agc acc gra ggg       432
Lys Ala Gln Ser Gln Gly Arg Ile Leu Val Thr Gly Ser Thr Xaa Gly
        130                 135                 140 ctt cac ggt ctc cct ttt aat gag gtg tac tgt gcc agt aaa ttt gca       480
Leu His Gly Leu Pro Phe Asn Glu Val Tyr Cys Ala Ser Lys Phe Ala
145                 150                 155                 160 ata gag gga gca tgt gag agt ttg gcc gtc ctc ctg caa aac ttc aat       528
Ile Glu Gly Ala Cys Glu Ser Leu Ala Val Leu Leu Gln Asn Phe Asn
                165                 170                 175 atc cat gtc agt ctc att gag tgt ggt cca gtc aac aca gac ttc ctg       576
Ile His Val Ser Leu Ile Glu Cys Gly Pro Val Asn Thr Asp Phe Leu
        180                 185                 190 gtc aac atg cag aag gca gag ctt ggg aat act tct ctc caa cag gtt       624
Val Asn Met Gln Lys Ala Glu Leu Gly Asn Thr Ser Leu Gln Gln Val
            195                 200                 205 gat acc aag aca gtc agc ctc tat gaa aaa tac ctg cag cac tgt gac       672
Asp Thr Lys Thr Val Ser Leu Tyr Glu Lys Tyr Leu Gln His Cys Asp
    210                 215                 220 tct gtt ttc caa aac gca gca cag gac act gag gac att gta aag gta       720
Ser Val Phe Gln Asn Ala Ala Gln Asp Thr Glu Asp Ile Val Lys Val
225                 230                 235                 240 ttt cta gat gcc atc cag tcc ccc agc ccc acg ttc aga tat ttc acc       768
Phe Leu Asp Ala Ile Gln Ser Pro Ser Pro Thr Phe Arg Tyr Phe Thr
                245                 250                 255 agt ggt ggt gtt cca cct ctg acc caa ttg aag ata aca gag cca gat       816
Ser Gly Gly Val Pro Pro Leu Thr Gln Leu Lys Ile Thr Glu Pro Asp
        260                 265                 270 ggc tca cag tgc atc cgt gct atg agc aaa ata atc ttc tca gtt gag       864
Gly Ser Gln Cys Ile Arg Ala Met Ser Lys Ile Ile Phe Ser Val Glu
    275                 280                 285 gaa caa taa                                                           873
Glu Gln
    290

<210> SEQ ID NO 5
<211> LENGTH: 290
<212> TYPE: PRT
<213> ORGANISM: Seriola dumerili
<220> FEATURE:
<221> NAME/KEY: misc_feature
<222> LOCATION: (109)..(109)
<223> OTHER INFORMATION: The 'Xaa' at location 109 stands for Ile.
<220> FEATURE:
<221> NAME/KEY: misc_feature
<222> LOCATION: (143)..(143)
<223> OTHER INFORMATION: The 'Xaa' at location 143 stands for Gly, or
      Glu.

<400> SEQUENCE: 5

Met Asp Lys Lys Val Val Leu Ile Thr Gly Cys Ser Ser Gly Ile Gly
1               5                   10                  15

Leu Ser Leu Ala Val Arg Leu Ala Ser Asp Pro Glu Lys Thr Phe Lys
            20                  25                  30

Val Tyr Ala Thr Met Arg Asn Leu Ala Lys Lys Glu Arg Leu Leu Glu
        35                  40                  45

Cys Val Lys Gly Leu His Lys Asp Thr Leu Asp Ile Leu Gln Met Asp
    50                  55                  60

Val Thr Asp Arg Gln Ser Ile Leu Asp Ala Arg Asp Arg Val Val Glu
65                  70                  75                  80
```

```
Lys Arg Leu Asp Ile Leu Val Cys Asn Ala Gly Val Gly Leu Met Gly
                85                  90                  95

Pro Leu Glu Leu Gln Ser Ser Asp Ser Met Arg Gln Xaa Leu Glu Val
            100                 105                 110

Asn Ile Leu Gly Thr Ile Gln Thr Ile Gln Ala Phe Leu Pro Glu Met
        115                 120                 125

Lys Ala Gln Ser Gln Gly Arg Ile Leu Val Thr Gly Ser Thr Xaa Gly
    130                 135                 140

Leu His Gly Leu Pro Phe Asn Glu Val Tyr Cys Ala Ser Lys Phe Ala
145                 150                 155                 160

Ile Glu Gly Ala Cys Glu Ser Leu Ala Val Leu Leu Gln Asn Phe Asn
                165                 170                 175

Ile His Val Ser Leu Ile Glu Cys Gly Pro Val Asn Thr Asp Phe Leu
            180                 185                 190

Val Asn Met Gln Lys Ala Glu Leu Gly Asn Thr Ser Leu Gln Gln Val
        195                 200                 205

Asp Thr Lys Thr Val Ser Leu Tyr Glu Lys Tyr Leu Gln His Cys Asp
    210                 215                 220

Ser Val Phe Gln Asn Ala Ala Gln Asp Thr Glu Asp Ile Val Lys Val
225                 230                 235                 240

Phe Leu Asp Ala Ile Gln Ser Pro Ser Pro Thr Phe Arg Tyr Phe Thr
                245                 250                 255

Ser Gly Gly Val Pro Pro Leu Thr Gln Leu Lys Ile Thr Glu Pro Asp
            260                 265                 270

Gly Ser Gln Cys Ile Arg Ala Met Ser Lys Ile Ile Phe Ser Val Glu
        275                 280                 285

Glu Gln
    290

<210> SEQ ID NO 6
<211> LENGTH: 180
<212> TYPE: DNA
<213> ORGANISM: Seriola dumerili
<220> FEATURE:
<221> NAME/KEY: exon
<222> LOCATION: (1)..(180)
<223> OTHER INFORMATION: r=a or g, s=c or g

<400> SEQUENCE: 6 tgt gta atg ctg gtg tgg gtt tga tgg ggc ccc tgg agc tgc agt cct    48
Cys Val Met Leu Val Trp Val     Trp Gly Pro Trp Ser Cys Ser Pro
1               5                       10                  15 cgg act cga tga ggc aaa tyt tgg agg tca aca tct tag gta cca tcc    96
Arg Thr Arg     Gly Lys Xaa Trp Arg Ser Thr Ser     Val Pro Ser
                    20                  25 aga cca tcc agg ctt tcc tac cag aga tga agg ctc aga gcc agg gcc   144
Arg Pro Ser Arg Leu Ser Tyr Gln Arg     Arg Leu Arg Ala Arg Ala
30                  35                      40 gca ttc tgg tca cgg gca gca ccg rag ggc ttc acg                   180
Ala Phe Trp Ser Arg Ala Ala Pro Xaa Gly Phe Thr
45                  50                  55

<210> SEQ ID NO 7
<211> LENGTH: 873
<212> TYPE: DNA
<213> ORGANISM: Seriola lalandi
<220> FEATURE:
<221> NAME/KEY: CDS
<222> LOCATION: (1)..(873)
<223> OTHER INFORMATION: r=a or g, s=c or g
```

<400> SEQUENCE: 7

```
atg gac aag aag gtg gtg ctg atc aca ggc tgc tcy tcg gga atc ggc      48
Met Asp Lys Lys Val Val Leu Ile Thr Gly Cys Xaa Ser Gly Ile Gly
1               5                   10                  15 ctc agc ctg gct gtc cgt ctg gca tct gac cct gaa aaa aca ttc aaa      96
Leu Ser Leu Ala Val Arg Leu Ala Ser Asp Pro Glu Lys Thr Phe Lys
                20                  25                  30 gtc tat gcc aca atg agg aac ctg gcc aag aaa gag cgt ctt tta gag     144
Val Tyr Ala Thr Met Arg Asn Leu Ala Lys Lys Glu Arg Leu Leu Glu
            35                  40                  45 tgt gtg aaa ggc ctg cac aaa gac acc ttg gac att ctc caa atg gat     192
Cys Val Lys Gly Leu His Lys Asp Thr Leu Asp Ile Leu Gln Met Asp
        50                  55                  60 gtg acg gac cgg cag tca att ctg gat gcg agg gac agg gtt gtg gag     240
Val Thr Asp Arg Gln Ser Ile Leu Asp Ala Arg Asp Arg Val Val Glu
65                  70                  75                  80 aaa cga ctg gac att ctg gtg tgt aat gct ggt gtg ggt ttg atg ggg     288
Lys Arg Leu Asp Ile Leu Val Cys Asn Ala Gly Val Gly Leu Met Gly
                85                  90                  95 ccc ctg gag ctg cag tcc tcg gac wcg atg agg caa att ttg gag gtc     336
Pro Leu Glu Leu Gln Ser Ser Asp Xaa Met Arg Gln Ile Leu Glu Val
                100                 105                 110 aac atc tta ggt acc atc cag acc atc cag gct ttc cta cca gag atg     384
Asn Ile Leu Gly Thr Ile Gln Thr Ile Gln Ala Phe Leu Pro Glu Met
            115                 120                 125 aag gct cag agc cag ggc cgc att ctg gtc acg ggc agc acc gra ggg     432
Lys Ala Gln Ser Gln Gly Arg Ile Leu Val Thr Gly Ser Thr Xaa Gly
        130                 135                 140 ctt cac ggt ctc cct ttt aat gag gtg tac tgt gcc agt aaa ttt gca     480
Leu His Gly Leu Pro Phe Asn Glu Val Tyr Cys Ala Ser Lys Phe Ala
145                 150                 155                 160 ata gag gga gca tgt gag agt ttg gcc gtc ctc ctg caa aac ttc aat     528
Ile Glu Gly Ala Cys Glu Ser Leu Ala Val Leu Leu Gln Asn Phe Asn
                165                 170                 175 atc cat gtc agt ctc att gag tgt ggt ccr gty aac aca gac ttc ctg     576
Ile His Val Ser Leu Ile Glu Cys Gly Xaa Xaa Asn Thr Asp Phe Leu
            180                 185                 190 gtc aac atg cag aag gcg gag ctt ggg aat act tct ctc caa cag gtt     624
Val Asn Met Gln Lys Ala Glu Leu Gly Asn Thr Ser Leu Gln Gln Val
        195                 200                 205 gat acc aag aca gtc agc ctc tat gaa aaa tac ctg cag cac tgt gac     672
Asp Thr Lys Thr Val Ser Leu Tyr Glu Lys Tyr Leu Gln His Cys Asp
    210                 215                 220 tct gtt ttc caa aac gca gca cag gac act gag gac att gta aag gta     720
Ser Val Phe Gln Asn Ala Ala Gln Asp Thr Glu Asp Ile Val Lys Val
225                 230                 235                 240 ttt cta gat gcc atc cag tca ccc agc ccc acg ttc aga tat ttc acc     768
Phe Leu Asp Ala Ile Gln Ser Pro Ser Pro Thr Phe Arg Tyr Phe Thr
                245                 250                 255 agt ggt ggt gtt cca cct cta acc caa ctg aag ata aca gag cca gat     816
Ser Gly Gly Val Pro Pro Leu Thr Gln Leu Lys Ile Thr Glu Pro Asp
            260                 265                 270 ggc tca cag tgc gtc cgt gct atg agc aaa ata atc ttc tca gtt gag     864
Gly Ser Gln Cys Val Arg Ala Met Ser Lys Ile Ile Phe Ser Val Glu
        275                 280                 285 gaa caa taa                                                          873
Glu Gln
    290
```

<210> SEQ ID NO 8
<211> LENGTH: 290
<212> TYPE: PRT
<213> ORGANISM: Seriola lalandi
<220> FEATURE:
<221> NAME/KEY: misc_feature
<222> LOCATION: (12)..(12)
<223> OTHER INFORMATION: The 'Xaa' at location 12 stands for Ser.
<220> FEATURE:
<221> NAME/KEY: misc_feature
<222> LOCATION: (105)..(105)
<223> OTHER INFORMATION: The 'Xaa' at location 105 stands for Thr, or Ser.
<220> FEATURE:
<221> NAME/KEY: misc_feature
<222> LOCATION: (143)..(143)
<223> OTHER INFORMATION: The 'Xaa' at location 143 stands for Gly, or Glu.
<220> FEATURE:
<221> NAME/KEY: misc_feature
<222> LOCATION: (186)..(186)
<223> OTHER INFORMATION: The 'Xaa' at location 186 stands for Pro.
<220> FEATURE:
<221> NAME/KEY: misc_feature
<222> LOCATION: (187)..(187)
<223> OTHER INFORMATION: The 'Xaa' at location 187 stands for Val.

<400> SEQUENCE: 8

Met Asp Lys Lys Val Val Leu Ile Thr Gly Cys Xaa Ser Gly Ile Gly
1               5                   10                  15

Leu Ser Leu Ala Val Arg Leu Ala Ser Asp Pro Glu Lys Thr Phe Lys
            20                  25                  30

Val Tyr Ala Thr Met Arg Asn Leu Ala Lys Lys Glu Arg Leu Leu Glu
        35                  40                  45

Cys Val Lys Gly Leu His Lys Asp Thr Leu Asp Ile Leu Gln Met Asp
    50                  55                  60

Val Thr Asp Arg Gln Ser Ile Leu Asp Ala Arg Asp Arg Val Val Glu
65                  70                  75                  80

Lys Arg Leu Asp Ile Leu Val Cys Asn Ala Gly Val Gly Leu Met Gly
                85                  90                  95

Pro Leu Glu Leu Gln Ser Ser Asp Xaa Met Arg Gln Ile Leu Glu Val
            100                 105                 110

Asn Ile Leu Gly Thr Ile Gln Thr Ile Gln Ala Phe Leu Pro Glu Met
        115                 120                 125

Lys Ala Gln Ser Gln Gly Arg Ile Leu Val Thr Gly Ser Thr Xaa Gly
    130                 135                 140

Leu His Gly Leu Pro Phe Asn Glu Val Tyr Cys Ala Ser Lys Phe Ala
145                 150                 155                 160

Ile Glu Gly Ala Cys Glu Ser Leu Ala Val Leu Leu Gln Asn Phe Asn
                165                 170                 175

Ile His Val Ser Leu Ile Glu Cys Gly Xaa Xaa Asn Thr Asp Phe Leu
            180                 185                 190

Val Asn Met Gln Lys Ala Glu Leu Gly Asn Thr Ser Leu Gln Gln Val
        195                 200                 205

Asp Thr Lys Thr Val Ser Leu Tyr Glu Lys Tyr Leu Gln His Cys Asp
    210                 215                 220

Ser Val Phe Gln Asn Ala Ala Gln Asp Thr Glu Asp Ile Val Lys Val
225                 230                 235                 240

Phe Leu Asp Ala Ile Gln Ser Pro Ser Pro Thr Phe Arg Tyr Phe Thr
                245                 250                 255

Ser Gly Gly Val Pro Pro Leu Thr Gln Leu Lys Ile Thr Glu Pro Asp

```
                    260                 265                 270
Gly Ser Gln Cys Val Arg Ala Met Ser Lys Ile Ile Phe Ser Val Glu
            275                 280                 285

Glu Gln
    290

<210> SEQ ID NO 9
<211> LENGTH: 180
<212> TYPE: DNA
<213> ORGANISM: Seriola lalandi
<220> FEATURE:
<221> NAME/KEY: exon
<222> LOCATION: (1)..(180)
<223> OTHER INFORMATION: r=a or g, s=c or g

<400> SEQUENCE: 9 tgt gta atg ctg gtg tgg gtt tga tgg ggc ccc tgg agc tgc agt cct       48
Cys Val Met Leu Val Trp Val     Trp Gly Pro Trp Ser Cys Ser Pro
1               5                   10                  15 cgg acw cga tga ggc aaa ttt tgg agg tca aca tct tag gta cca tcc       96
Arg Xaa Arg     Gly Lys Phe Trp Arg Ser Thr Ser     Val Pro Ser
            20                  25 aga cca tcc agg ctt tcc tac cag aga tga agg ctc aga gcc agg gcc      144
Arg Pro Ser Arg Leu Ser Tyr Gln Arg     Arg Leu Arg Ala Arg Ala
30              35                  40 gca ttc tgg tca cgg gca gca ccg rag ggc ttc acg                      180
Ala Phe Trp Ser Arg Ala Ala Pro Xaa Gly Phe Thr
45              50                  55

<210> SEQ ID NO 10
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 10
atgccacaat gaggaacctg                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 11
actcagggtg caagatgcag                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 12
taccagagat gaaggctcag                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Sequence
```

```
<400> SEQUENCE: 13
catttgcttg tctcaccgtg                                              20

<210> SEQ ID NO 14
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 14
ctggtcacrg gsagcaccgr agggcttcac g                                 31

<210> SEQ ID NO 15
<211> LENGTH: 33
<212> TYPE: DNA
<213> ORGANISM: Seriola sp.

<400> SEQUENCE: 15
ctggtcacgg gcagcaccgr agggcttcac ggt                               33

<210> SEQ ID NO 16
<211> LENGTH: 33
<212> TYPE: DNA
<213> ORGANISM: Seriola lalandi

<400> SEQUENCE: 16
ctggtcacgg gcagcaccgg agggcttcac ggt                               33

<210> SEQ ID NO 17
<211> LENGTH: 33
<212> TYPE: DNA
<213> ORGANISM: Seriola quinqueradiata

<400> SEQUENCE: 17
ctggtcacrg gsagcaccgr agggcttcac ggt                               33

<210> SEQ ID NO 18
<211> LENGTH: 33
<212> TYPE: DNA
<213> ORGANISM: Seriola dumerili

<400> SEQUENCE: 18
ctggtcacgg gcagcaccga agggcttcac ggt                               33

<210> SEQ ID NO 19
<211> LENGTH: 33
<212> TYPE: DNA
<213> ORGANISM: Seriola quinqueradiata

<400> SEQUENCE: 19
ctggtcacag ggagcaccga agggcttcac ggt                               33
```